United States Patent [19]
Patel

[11] Patent Number: 6,133,457
[45] Date of Patent: Oct. 17, 2000

[54] PROCESS FOR PREPARING PHARMACEUTICAL COMPOUNDS

[75] Inventor: Vinod F Patel, Carmel, Ind.

[73] Assignees: Eli Lilly and Company, Indianapolis, Ind.; Wayne State University, Detroit, Mich.; University of Hawaii, Honolulu, Hi.

[21] Appl. No.: 09/346,844

[22] Filed: Jul. 2, 1999

Related U.S. Application Data

[62] Division of application No. 09/029,202, filed as application No. PCT/US97/14800, Aug. 25, 1997, Pat. No. 5,977,387
[60] Provisional application No. 60/038,983, Feb. 26, 1997, and provisional application No. 60/025,082, Aug. 30, 1996.

[51] Int. Cl.[7] .................... C07D 207/40; C07D 207/416; C07D 303/16; C07D 303/36
[52] U.S. Cl. .................... 548/547; 548/542; 549/553; 549/554
[58] Field of Search .................... 548/547, 542; 549/554, 553

[56] References Cited

FOREIGN PATENT DOCUMENTS

| 861 838 A2 | 2/1998 | European Pat. Off. ...... C07D 413/06 |
| WO 96/40184 | 3/1996 | WIPO ............................. A61K 38/00 |
| WO 97/07798 | 8/1996 | WIPO ............................. A61K 31/395 |
| WO 98/08506 | 8/1997 | WIPO ............................. A61K 31/395 |
| WO 98/08829 | 8/1997 | WIPO ............................. A61K 31/395 |
| WO 98/38178 | 2/1998 | WIPO ............................. A61K 31/395 |

OTHER PUBLICATIONS

Russell A. Barrow, et al., Total Synthesis of Cryptophycins. Revision of the Structures of Cryptophycins A and C. *J. Am. Chem. Soc.* (1995), 117, 2479–2490.

*Primary Examiner*—Ba K. Trinh
*Attorney, Agent, or Firm*—John H. Engelmann; MaCharri Vorndran-Jones

[57] ABSTRACT

A compound of formula IV

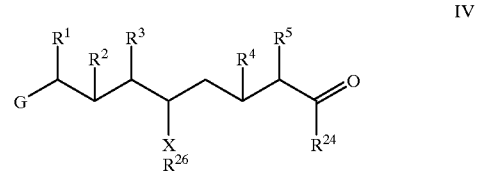

wherein

G is $C_1$–$C_{12}$ alkyl, $C_2$–$C_{12}$ alkenyl, $C_2$–$C_{12}$ alkynyl or Ar;

Ar is an aromatic or heteroaromatic group or a substituted aromatic or heteroaromatic group;

$R^1$ is halo, SR, OR, amino, mono or di-($C_1$–$C_6$-alkyl) amino, tri ($C_1$–$C_6$-alkyl)ammonium, $C_1$–$C_6$-alkylthio, di($C_1$–$C_6$-alkyl)sulfonium, $C_1$–$C_6$-alkylsulfonyl, or $C_1$–$C_6$-alkylphosphonyl;

$R^2$ is OH or SH; or $R^1$ and $R^2$ taken together form a second bond or together form an epoxide, aziridine, episulfide, or cyclopropyl ring;

R is H, $C_1$–$C_6$ alkyl, $C_1$–$C_6$ alkanoyl or Ar;

$R^3$ is $C_1$–$C_6$ alkyl;

$R^4$ and $R^5$ are H; or $R^4$ and $R^5$ taken together form a second bond;

$R^{24}$ is a leaving group; and $R^{26}$ is an alcohol protecting group;

X is O, NH or (C1–C3 alkyl)N—.

5 Claims, No Drawings

PROCESS FOR PREPARING PHARMACEUTICAL COMPOUNDS

This application is a divisional of Ser. No. 09/029,202 filed on Feb. 25, 1998, was U.S. Pat. No. 5,977,387 which is a 371 of PCT/US97/14800 filed Aug. 25, 1997. This application also claims the priority benefit of provisional application 60/038,983 filed Feb. 26, 1997 and 60/025,082 filed Aug. 30, 1996.

This invention relates to the fields of pharmaceutical and organic chemistry and provides novel cryptophycin compounds, intermediates for the preparation of other cryptophycin compounds and a novel process for the preparation of cryptophycin compounds having antimicrotubule activity.

Antimetabolites have been used for a number of years as chemotherapeutic agents in the treatment of cancer. A new class of antimetabolites, cryptophycin compounds, are useful for disrupting the microtubule system. In order to produce sufficient quantities of these compounds, efficient totally synthetic processes for the preparation of cryptophycin compounds are desired.

The present invention provides a rapid analog process and key intermediates for the total synthesis of cryptophycin compounds. The cryptophycin compounds prepared by this process are useful for disrupting the microtubule system of eucaryotic cells and are also useful research tools.

The present invention provides novel intermediate compounds of formula II

II wherein
G is $C_1$–$C_{12}$ alkyl, $C_2$–$C_{12}$ alkenyl, $C_2$–$C_{12}$ alkynyl or Ar;
Ar is an aromatic or heteroaromatic group or a substituted aromatic or heteroaromatic group;
$R^1$ is halo, SR, OR, amino, mono or di-($C_1$–$C_6$-alkyl)amino, tri($C_1$–$C_6$-alkyl)ammonium, $C_1$–$C_6$-alkylthio, di($C_1$–$C_6$-alkyl)sulfonium, $C_1$–$C_6$-alkylsulfonyl, or $C_1$–$C_6$-alkylphosphonyl; and
$R^2$ is OH or SH; or
$R^1$ and $R^2$ taken together form a second bond between C-18 and C-19 or together form an epoxide, aziridine, episulfide, or cyclopropyl ring;
R is H, $C_1$–$C_6$ alkyl, $C_1$–$C_6$ alkanoyl or Ar;
$R^3$ is $C_1$–$C_6$ alkyl;
$R^4$ and $R^5$ are H; or
$R^4$ and $R^5$ taken together form a second bond between C-13 and C-14;
$R^7$ is H, $C_1$–$C_6$ alkyl $NR^5R^{52}$, —($C_1$–$C_3$-alkyl)$NR^{51}R^{52}$, or $OR^{51}$; and
$R^8$ is H or $C_1$–$C_6$ alkyl; or
$R^7$ and $R^8$ together form a cyclopropyl ring;
$R^{51}$ and $R^{52}$ independently are $C_1$–$C_3$ alkyl;
$R^9$ is H, $C_1$–$C_6$ alkyl, $C_2$–$C_6$ alkenyl, $C_2$–$C_6$-alkynyl or ($C_1$–$C_6$ alkyl) $C_3$–$C_5$ cycloalkyl;
$R^{10}$ is H or $C_1$–$C_6$ alkyl;
$R^{13}$ is an amino protecting group;
$R^{24}$ is a leaving group;
X is O, NH or ($C_1$–$C_3$ alkyl)N—; and
Y is C, O, NH, S, SO, $SO_2$ or ($C_1$–$C_3$ alkyl)N—.

Another aspect of this invention are novel intermediates of formula IV

IV wherein G, X, $R^1$, $R^2$, $R^3$, $R^4$, $R^5$, and $R^{24}$ are as defined supra, and $R^{26}$ is an alcohol protecting group.

This invention also provides a process for preparing a compound of formula III

III wherein G, X, Y, $R^1$, $R^2$, $R^3$, $R^4$, $R^5$, $R^6$, $R^7$, $R^8$, $R^9$, $R^{10}$ and $R^{13}$ are as defined supra, and $R^6$ is $C_1$–$C_6$ alkyl, substituted ($C_1$–$C_6$)alkyl, ($C_3$–$C_8$)cycloalkyl, substituted $C_3$–$C_8$ cycloalkyl, a heteroaromatic or substituted heteroaromatic group, or a group of formula IIIa, III' or III":

IIIa

III'

III"

wherein
$R^{6a}$, $R^{6b}$, and $R^{6c}$ independently are H, halo or $OR^{18}$;
$R^{15}$, $R^{16}$, and $R^{17}$ independently are hydrogen, halo, ($C_1$–$C_6$) alkyl, $OR^{18}$, O-aryl, $NH_2$, $NR^{18}R^{19}$, $NO_2$, $OPO_4H_2$, ($C_1$–$C_6$ alkoxy)phenyl, Sbenzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;

$R^{23}$ is hydrogen or $(C_1$–$C_3)$alkyl;

Z is —$(CH_2)_n$— or $(C_3$–$C_5)$ cycloalkyl;

n is 0, 1, or 2; and

Z' is an aromatic or substituted aromatic group;

Comprising Contacting (a) a compound of formula II with a compound of formula V

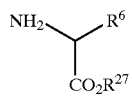

V wherein $R^{27}$ is H, Ar, $C_1$–$C_{12}$ alkyl, or $C_1$–$C_6$ alkyl having up to three substituents selected from halo, $C_1$–$C_3$ alkoxy and $C_1$–$C_3$ alkylthio;

in the presence of a silylating agent.

Another embodiment of this invention is a process for preparing a compound of Formula I

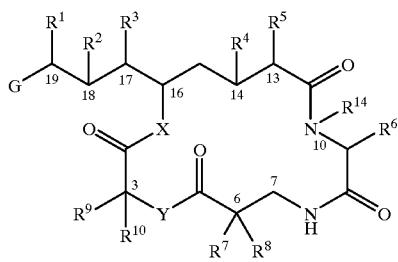

I wherein G, X, Y, $R^1$, $R^2$, $R^3$, $R^4$, $R^5$, $R^6$, $R^7$, $R^8$, $R^9$ and $R^{10}$ are as defined supra; and $R^{14}$ is H or a lower alkyl group;

Comprising (a) contacting a compound of formula II as defined supra with a compound of formula V as defined supra, in the presence of a silylating agent;

(b) removing the R group;

(c) cyclizing the product of step b;

(d) optionally derivitizing the product of step c; and (e) optionally forming a salt of the product of step c or step d.

The processes of this invention provide a means for preparing cryptophycin compounds by a totally synthetic route. With these processes, commercially available amino acids can be cyclized into the cryptophycin molecule. Additionally, the processes provided herein are shorter and more efficient than previously known total synthetic methods. See Barrow, et al. *J. Am. Chem. Soc.* 1995, 117, 2479–2490.

As used herein, the term "alkyl" refers to an alkyl group with the designated number of carbon atoms. It may be saturated or unsaturated, and branched or straight chain. "Lower alkyl" means a $C_1$–$C_5$ alkyl group. Examples of such alkyl groups include methyl, ethyl, n-propyl, isopropyl, n-butyl, propenyl, sec-butyl, n-pentyl, isobutyl, tert-butyl, sec-butyl, methyl-substituted butyl groups, pentyl, tert-pentyl, sec-pentyl, methyl-substituted pentyl groups and the like.

"Substituted alkyl" refers to a $C_1$–$C_6$ alkyl group that may include up to three (3) substituents containing one or more heteroatoms. Examples of such substituents are OH, Sbenzyl, $NH_2$, $CONH_2$, $CO_2H$, $PO_3H_2$ and $SO_2R^{21}$ wherein $R^{21}$ is hydrogen or $C_1$–$C_3$ alkyl.

The term "cycloalkyl" refers to a saturated $C_3$–$C_8$ cycloalkyl group. A "substituted cycloalkyl group" refers to a cycloalkyl group having up to three $C_1$–$C_3$ alkyl, halo, or $OR^{21}$ substituents. The substituents may be attached at any available carbon atom. Cyclohexyl is an especially preferred cycloalkyl group.

"Lower alkoxy" means a $C_1$–$C_5$ alkyl group bonded to an oxygen atom.

The terms "aromatic group" and "heteroaromatic group" refer to common aromatic rings having 4n+2 pi electrons in a monocyclic conjugated system or a bicyclic conjugated system. The term "aryl" refers to an aromatic group. Examples of aromatic groups are phenyl, benzyl and naphthyl. Heteroaromatic groups will contain one or more oxygen, nitrogen and/or sulfur atoms in the ring. Examples of heteroaromatic groups include furyl, pyrrolyl, thienyl, pyridyl and the like. When the aromatic or heteroaromatic groups are substituted, they may have from one to three independently selected $C_1$–$C_7$ alkyl or halo substituents. The substituents may be attached at any available carbon atom.

The term "halo" refers to Cl, Br, F, or I. Especially preferred heterocyclic groups are

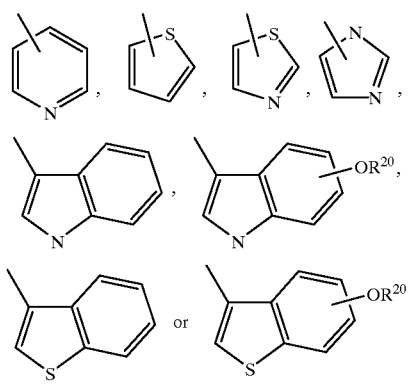

wherein $R^{20}$ is hydrogen or $C_1$–$C_6$ alkyl.

The term "amino protecting group" refers to a standard amino protecting group that is either acid labile or can be removed under mildly basic to neutral conditions. Such groups are well known in the art. [See, for example, "Protective Groups in Organic Chemistry", Plenum Press, (London and New York, 1973); Greene, T. W. "Protecting Groups in Organic Synthesis", Wiley (New York, 1981)]. Preferred amino protecting groups are acid labile. An especially preferred amino protecting group is tert-butoxycarbonyl ("BOC"). When the $R^6$ substituent in a Formula I compound contains an amino substituent, it must be protected using an amino protecting group.

The term "leaving group" is also well understood in the art. Such groups involve an active ester that can be selected with guidance from the standard references for protecting groups such as, for example, the references named supra. An especially preferred leaving group is N-hydroxysuccinimidyl (NHS). N-Hydroxysulfosuccinimdyl, or a salt thereof, 2-nitrophenyl, 4-nitrophenyl and 2,4-dichlorophenyl are also examples of useful leaving groups.

An "alcohol protecting group" is one that is introduced during a portion of the synthetic process to protect an alcohol group that might otherwise react in the course of chemical manipulations. The group is then removed at a later stage of the synthesis. Reactions for the formation and removal of such protecting groups are described in a number of standard works, including the two references listed supra. A particularly useful alcohol protecting group is tert-butyldimethylsilyl (TBS).

The processes of this invention are preferably carried out in the presence of a solvent. Selection of an appropriate solvent is commonly understood in the art. An inert organic solvent, such as N,N-dimethylformamide (DMF), ethyl acetate, methylene chloride, toluene or acetonitrile, or a mixture thereof, is recommended. Under certain conditions an aqueous solvent can be appropriate. For example, if $R^{27}$ is hydrogen and $R^{13}$ is BSA (defined infra), an aqueous solvent will be effective. An especially preferred solvent is DMF.

$R^{27}$ should be a group that allows for the removal of the $—CO_2R^{27}$ substituent using acidic, neutral, or mild basic conditions. Preferred $R^{27}$ groups include hydrogen, $C_1-C_6$ alkyl, trichloromethyl, trichloroethyl, and methylthiomethyl. Hydrogen is especially preferred.

"Epoxide ring" means a three-membered ring whose backbone consists of two carbon and one oxygen atoms. "Aziridine ring" means a three-membered ring whose backbone consists of two carbon and one nitrogen atoms. "Episulfide ring" refers to a three-membered ring whose backbone consists of two carbon and one sulfur atoms. "Sulfate group" means a five-membered ring consisting of a carbon—carbon—oxygen—sulfur—oxygen backbone with two additional oxygen atoms connected to the sulfur atom. "Monalkylphosphate ring" means a five-membered ring consisting of a carbon—carbon— oxygen—phosphorous—oxygen backbone with two additional oxygen atoms, one of which bears a lower alkyl group, connected to the phosphorous atom.

Examples of methods of halogenation include the addition of hydrogen halides, substitution at high temperature, photohalogenation, etc. Such methods are known in the art.

The term "derivitizing" refers to standard types chemical modifications of the product of step c that are needed to prepare the desired Formula I compounds. For example, the styrene can be derivitized to form the epoxide.

A "silylating agent" is any reagent capable of attaching a silyl group to a target substituent. Generally known silylating agents may be used. See for example, Calvin, E. W., "Silicon Reagents in Organic Synthesis", Academic Press, (London, 1988). Particularly useful silylating agents include "tri-lower alkyl silyl" agents, which include triisopropylsilyl, trimethylsilyl and triethylsilyl, trimethylsilyl halides, silylated ureas such as bis(trimethylsilyl)urea (BSU) and silylated amides such as bis(trimethylsilyl) acetamide (BSA). Of these, BSA is preferred. Other useful silylating agents are those with an alkylarylsilyl or arylsilyl group, such as tribenzylsilyl, diphenylmethylsilyl, t-butylmethoxyphenylsilyl, tri-(p-xylyl)silyl, and triphenylsilyl.

A preferred silylating agent is a trimethylsilylating agent. Typical trimethylsilylating agents include BSA; allyltrimethylsilane; N,O-bis(trimethylsilyl)carbamate; N,N-bis (trimethylsilyl)methylamine; bis(trimethylsilyl)sulfate; bis (trimethylsilyl)trifluoroacetamide; BSU [(ethylthio) trimethylsilane]; ethyl(trimethylsilyl)acetate; hexamethyldisilane; 1,1,1,3,3,3-hexamethyldisilazane; hexamethyldisiloxane; [hexamethyldisilthiane; (isopropenyloxy)trimethylsilane,]; (methoxymethyl) trimethylsilane; (methylthio)trimethylsilane; methyl 3-trimethylsiloxy-2-butenoate, N-methyl-N-trimethylsilylacetamide, methyl trimethylsilylacetate, N-methyl-N-trimethylsilyl-hepta-fluorobutyramide, N-methyl-N-trimethylsilyl-trifluoroacetamide, (phenylthio) trimethylsilane, trimethylbromosilane, trimethylchlorosilane, trimethyliodosilane, 4-trimethylsiloxy-3-penten-2-one, N-(trimethylsilyl) acetamide, trimethylsilyl acetate, trimethylsilyl azide, trimethylsilyl benzenesulfonate, trimethylsilyl cyanide, N-trimethylsilyldiethylamine, N-trimethylsilyldimethylamine, trimethylsilyl N,N-dimethylcarbamate, 1-(trimethylsilyl)imidazole, trimethylsilyl methanesulfonate, 4-(trimethylsilyl)morpholine, 3-trimethylsilyl-2-oxazolidinone, trimethylsilyl trichloroacetate, trimethylsilyl trifluoroacetate and trimethylsilyl trifluoromethane sulfonate.

The $R^{13}$ group can be removed using well known methods. For example, the reaction mixture can be acidified to prepare an amine salt. Trifluoroacetic acid is especially preferred for this purpose. If the amino protecting group is neutral labile or labile under mildly basic conditions, then the reaction mixture pH should be adjusted accordingly.

Likewise, the product of step (b) can be cyclized using known methods. For example, a preferred method is using N,N-diisopropylethylamine in the presence of an inert organic solvent, followed by treatment with pentafluorophenyl diphenylphosphinate.

Some preferred embodiments of this invention are those intermediates or processes when:

A) $R^8$ is ethyl, propyl, isopropyl, butyl, isobutyl or isopentyl;

B) $R^7$ is ethyl, propyl, isopropyl, butyl, isobutyl, pentyl, or isopentyl;

C) $R^7$ is H, $R^8$ is methyl, $R^3$ is methyl, and X and Y are not both 0;

D) $R^3$ is ethyl, propyl, isopropyl, butyl, isobutyl, pentyl or isopentyl;

E) $R^9$ is methyl, ethyl, propyl, butyl, isobutyl, pentyl, or isopentyl;

F) $R^{10}$ is methyl, ethyl, propyl, butyl, isobutyl, pentyl, or isopentyl;

G) the cryptophycin compound prepared is one wherein at least one of the groups at C-3, C-6, C-7, C-10, C-16, C-17, or C-18 has R stereochemistry (numbering as set forth in Formula I, supra);

H) the cryptophycin compound prepared is one wherein at least one of the groups at C-3, C-6, C-7, C-10, C-16, C-17, or C-18 has S stereochemistry;

I) the cryptophycin compound is one wherein the groups at C-3 and C-16 have S stereochemistry, the groups at C-6 and C-17 have R stereochemistry, and $R^1$ and $R^2$ form a β-epoxide ring;

J) Y is O, NH, S, SO or $SO_2$;

K) Y is C; $R^7$, $R^8$, $R^9$, and $R^{10}$ are hydrogen; and $R^1$ and $R^2$ form an epoxide ring;

L) $R^7$ and $R^8$ are hydrogen;

M) Y is O;

N) $R^1$ and $R^2$ form a β-epoxide ring;

O) both X and Y are O;

P) $R^4$ and $R^5$ form a double bond;

Q) $R^6$ is benzyl substituted with one halo and one $C_1-C_5$-alkoxy group;

R) Y is S;

S) Y is SO or $SO_2$;

T) $R^{13}$ is BOC;

U) $R^{24}$ is —NHS;

V) the silylating agent is BSA;

W) $R^{27}$ is H; and

X) Ar is phenyl or substituted phenyl.

To provide further guidance, the following schemes are provided. Certain abbreviations are used in the Schemes, Preparations and Examples. These abbreviations include:

| | |
|---|---|
| DMAP | 4-dimethylaminopyridine |
| BOC | tert-butoxycarbonyl |
| mcpba | m-chloroperbenzoic acid |
| TMSCl | chlorotrimethylsilane |
| HEW | Horner-Emmons-Wadsworth reaction (standard reaction for olefination of an aldehyde using a phosphonate and a base) |
| TMG | 1,1,3,3-tetramethylguanidine (standard base used for the HEW reaction) |
| DIBAL | diisobutylaluminum hydride (standard reagent for the reduction of an unsaturated ester to an allylic alcohol) |
| SAE | Sharpless Asymmetric Epoxidation (established reaction for the enantioselective epoxidation of allylic alcohols) |
| TBS | tert-butyldimethylsilyl |
| TBS-Otf | TBS trifluoromethanesulfonate (standard reagent for the t-butyldimethylsilylation of alcohols) |
| AIBN | 2,2'-azobis(isobutyronitrile) (standard radical initiator) |
| ACN | acetonitrile |
| DBU | 1,8-diazabicyclo[5.4.0]undec-7-ene (standard amine base) |
| EDCI | 1-ethyl-3-(3-dimethylaminopropyl)carbodiimide |

Scheme I

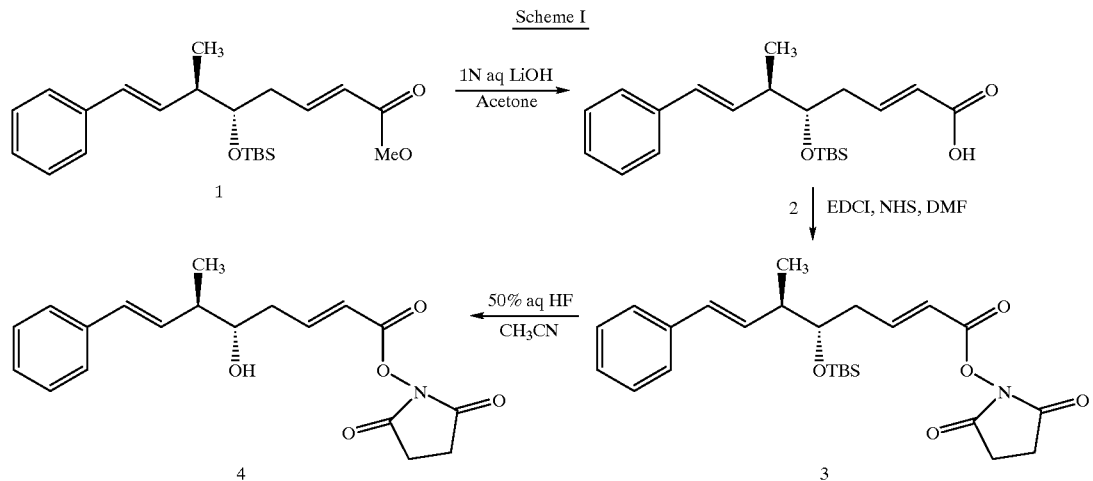

Scheme I'

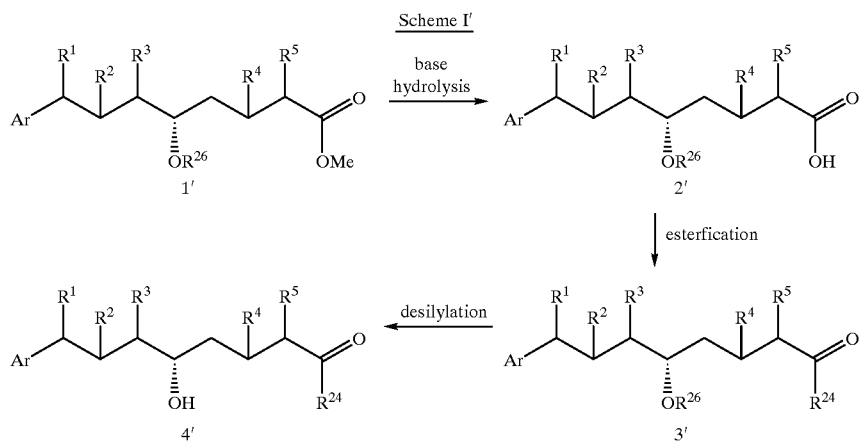

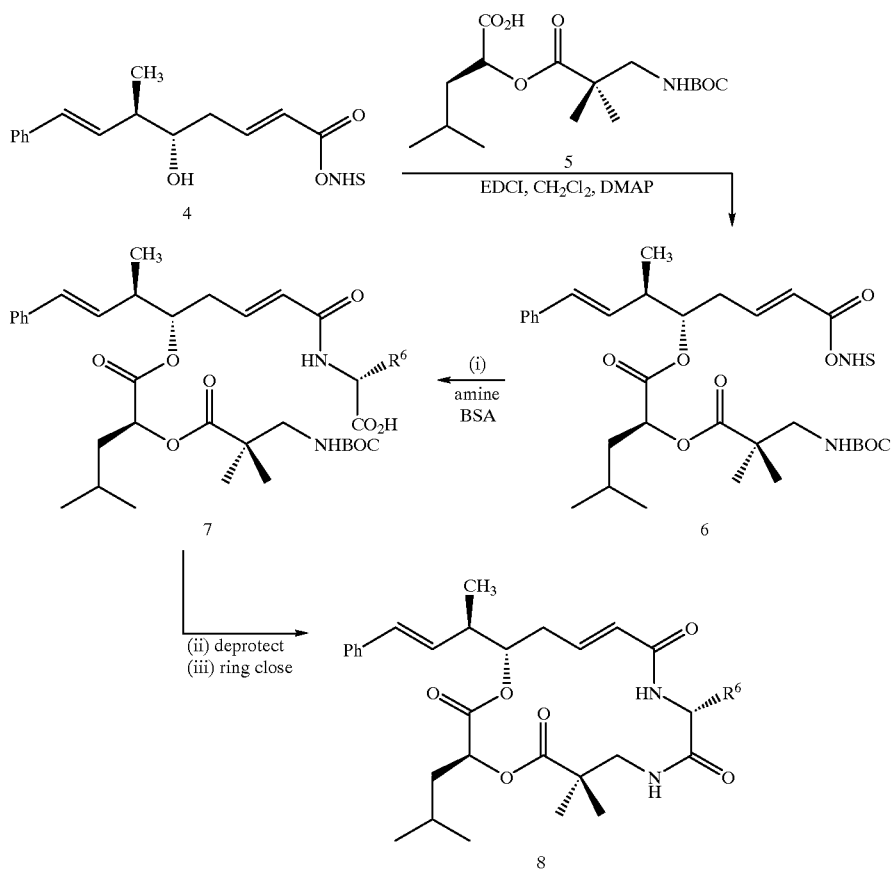
In Scheme 2, $R^6$ has the meaning defined supra.
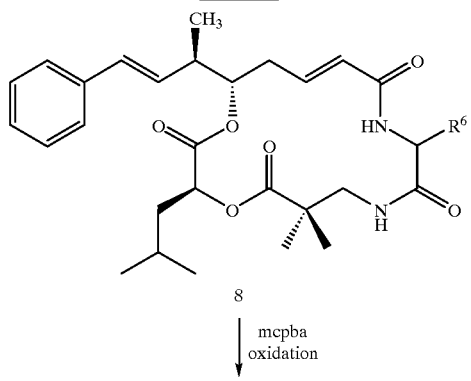

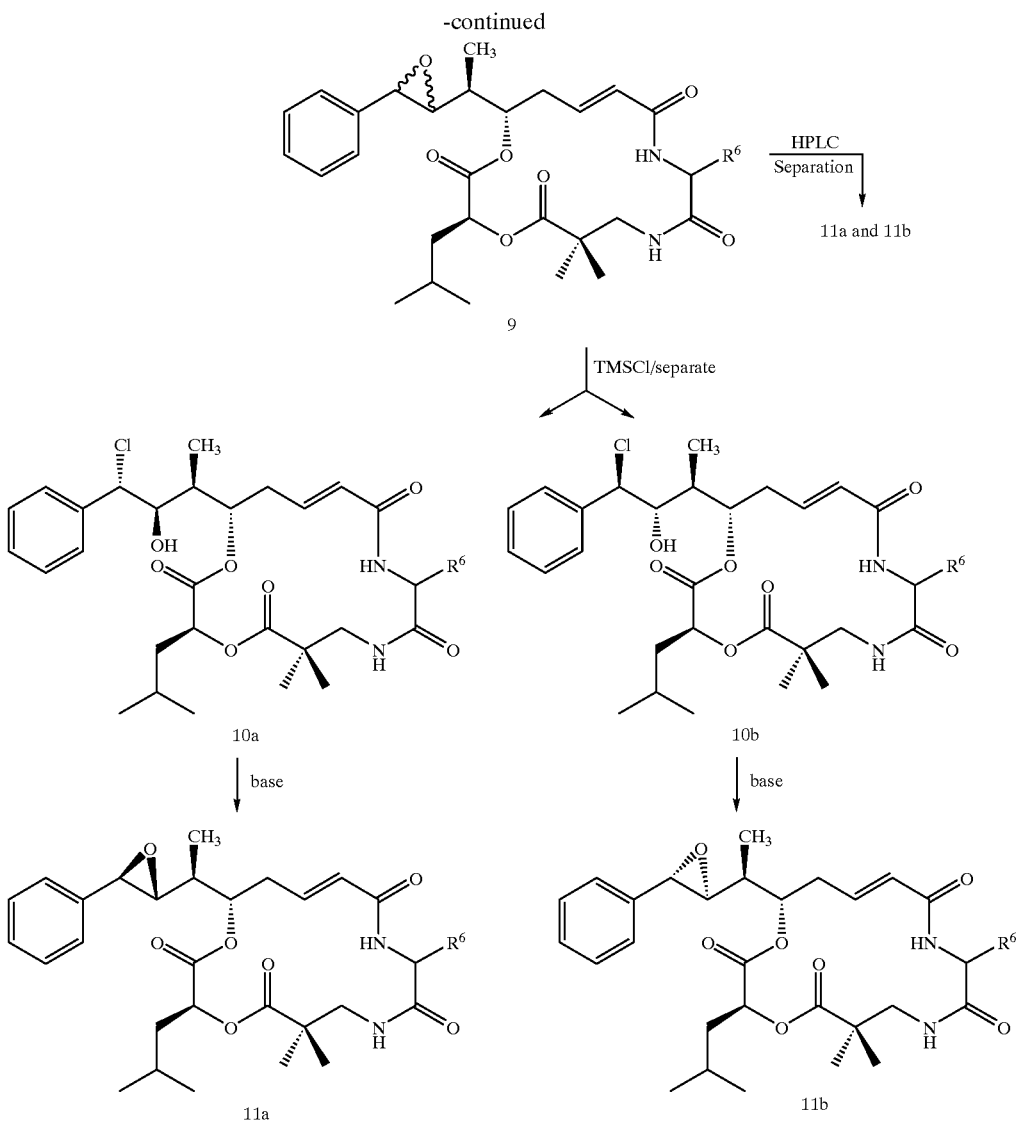

Appropriate starting materials and reagents can be used to prepare desired compounds using the guidance of the previous schemes and following examples.

The products illustrated in the schemes and examples provided herein can be further derivatized using standard methods to provide other cryptophycin compounds. Preparation of an ester 1'-type starting material is exemplified by the preparation of Compound 1, as follows:

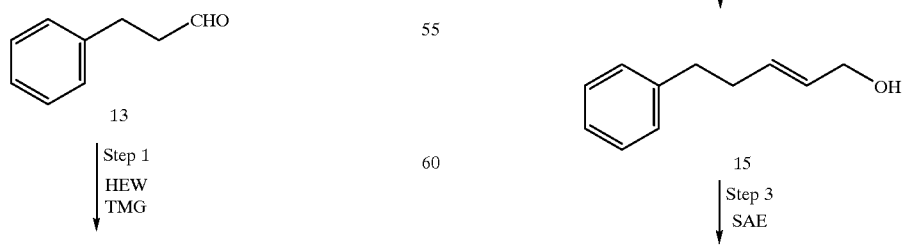

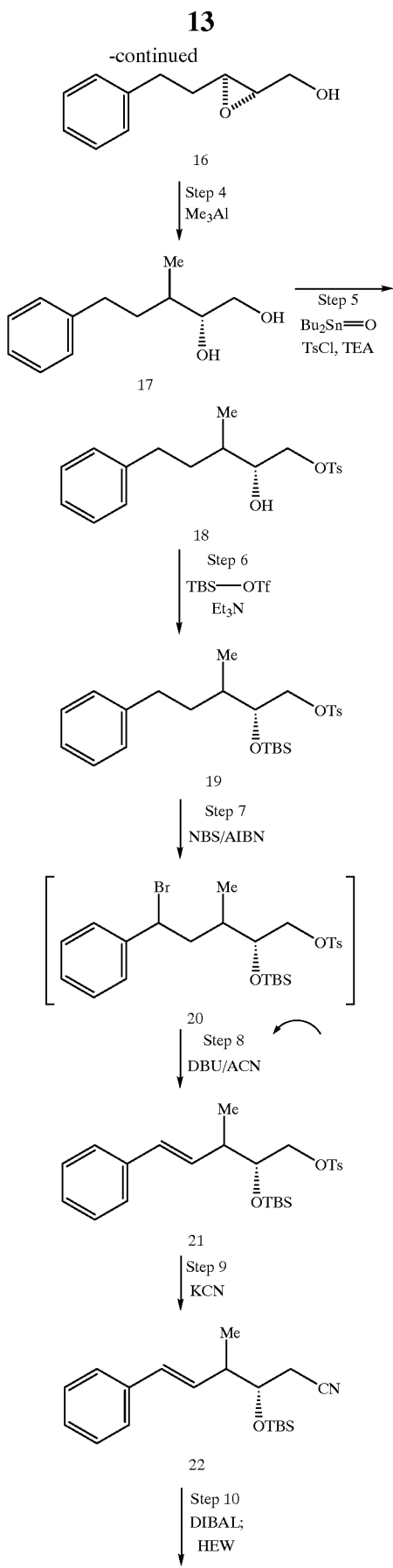

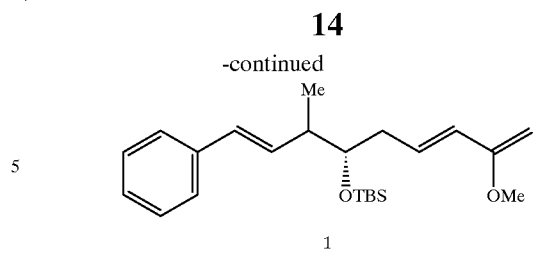

Further details for preparing ester 1 are set forth in the Preparation Section infra. Appropriate modifications can be used to prepare esters with various G substituents.

The necessary reaction times are related to the starting materials and operating temperatures. The optimum reaction time for a given process is, as always, a compromise which is determined by considering the competing goals of throughput, which is favored by short reaction times, and maximum yield, which is favored by long reaction times.

To further illustrate the invention the following non-limiting examples are provided.

Preparation 1

Step 1

Methyl 5-phenylpent-2(E)-enoate (14)

A solution of trimethyl phosphonoacetate (376 g, 417 mL, 2.07 mol) in THF (750 mL) was stirred at 0° C. in a 3 L 3-neck round-bottom flask equipped with a mechanical stirrer and $N_2$ inlet. To the chilled solution, neat 1,1,3,3-tetramethylguanidine (TMG) (239 g, 260 mL, 2.07 mol) was added dropwise via an addition funnel. The chilled clear pale yellow solution was stirred for 25 minutes at 0° C. A solution of hydrocinnamaldehyde (13) (90%, 253 g, 248 mL, 1.9 mol) in THF (125 mL) was added dropwise to the reaction solution slowly. Upon completion of addition, the reaction was stirred for 10 h rising to room temperature. GC indicated a 95:5 ratio of product to starting material. Water (500 ml) was added to the reaction vessel, and the reaction was stirred overnight, then separated into two layers. The organic layer was isolated, and the aqueous layer was extracted with t-BuOMe. The organic layers were combined and dried over $MgSO_4$, then concentrated in vacuo to yield an orange oil. The crude product was distilled at 129° C./0.3 mm Hg, yielding the title compound (360.5 g, 91.7% yield), as a clear, slightly yellow oil. EIMS m/z 190 (13; M+), 159 (410, 158 (39), 131 (90), 130 (62), 117 (22), 104 (12), 95 (57), 91 (100), 77 (21), 65 (59); HREIMS m/z 190-0998 ($C_{12}H_{14}O_2$ D −0.4 mnu); UV lmax (e) 210 (8400), 260 (230) nm; IR nmax 3027, 2949, 1723, 1658, 1454, 1319, 1203, 978, 700 $cm^{-1}$; $^1H$ NMR d ($CDCl_3$) 7.15–7.3 (Ph-H5;bm), 7.00 (3-H;dt, 15.6/6.6), 5.84 (2-H;dt, 15.6/1.2), 3.70 (OMe;s), 2.76 (5-H2;t, 7.2), 2.51 (4-H2; bdt, 6.6/7.2); $13_c$ NMR d ($CDCl_3$) 166.9 (1), 148.3 (3), 140.6 (Ph-1'), 128.4/128.2 (Ph2'/31/5'6'), 126.1 (Ph 4'), 121.4 (2). 51.3 (OMe), 34.2/33.8 (4/5).

Step 2

5-Phenyl-pent-2-en-1-ol (15)

To a 12 L 4-neck round-bottom flask equipped with a thermocouple, mechanical stirrer and $N_2$ inlet, a solution of enoate ester (14) (310.5 g, 1.5 mol) in THF (1.5 L) was charged and chilled to −71° C. via an i-PrOH/$CO_2$ bath. To the reaction vessel was added dropwise DIBAL (2.5 L, 1.5 M in toluene, 3.75 mol) at a rate to maintain the reaction temperature <−50° C. Upon complete addition, the reaction was stirred overnight with the reaction temperature <−50° C. TLC (3:1 Hexanes:EtOAc, $SiO_2$) indicated absence of starting material after 16 h. The reaction temperature was allowed to raise to −15° C. The reaction was quenched slowly with 1 N HCl (150 mL). At this point the reaction mixture became a gelatinous semi-solid. A spatula was used to breakup this semi-solid, and 1 N HCl (200 mL) was added, making the mixture more fluid. Concentrated HCl (625 mL) was charged to form a two phase system. The layers were separated, and the product extracted with t-BuOMe. The organic layer was dried over $MgSO_4$ and concentrated in vacuo to yield the title product as a clear pale yellow oil, 247.8 g. The crude product was distilled at 145° C./0.25 mm Hg, yielding 209.7 g, 86.2%. EIMS m/z 162 (1:M+) 144 (16), 129 (7), 117 (9) 108 (6), 92 (17), 91 (100), 75 (5), 65 (12), HREIMS m/z 162, 1049 ($C_{11}H_{14}O$, D −0.4 mmu); UV lmax (e) 206 (9900), 260 (360); IR nmax 3356, 2924, 1603, 1496, 1454, 970, 746, 700 $cm^{-1}$; $^1H$ NMR d 7.15–7.3 (Ph-H5;m), 5.70 (3-H;dt, 15.6/6.0), 5.61 (2H;dt, 15.6/4.8), 4.02 (1-H2;d 4.8), 2.68 (5-H2; t, 7.2), 2.40 (OH;bs), 2.36(4-H2; dt, 6.0/7.2); $^{13}C$ NMR d141.6 (Ph 1'), 131.8(3), 129.5 (2), 128.3/128.2 (Ph 2'/3'/5'/6'), 125.7 (Ph 4'), 63.3 (1), 35.4/33.8 (4/5).

Step 3

(2S,3S)-2,3-Epoxy-5-phenyl-1-pentanol (16)

To a 1 L 3-neck round-bottom flask equipped with a mechanical stirrer, thermocouple and nitrogen inlet was added $CH_2Cl_2$ (350 mL), dried 4 Å molecular sieves (30 g) and L-(+)-diethyl tartrate (7.62 g, 0.037 mol). The resulting mixture was cooled to −20° C. and treated with $Ti(O-i-Pr)_4$ (9.2 mL, 0.031 mol), followed by the addition of t-butylhydroperoxide (4.0 M in $CH_2Cl_2$, 182 mL, 0.78 mol) at a rate to maintain the temperature $^2$ −20° C. Upon complete addition, the reaction mixture was stirred for another 30 min, and then treated with a solution of the allylic alcohol (15) (50 g, 0.31 mol) in $CH_2Cl_2$ (30 mL) at a rate to maintain the temperature at −20° C. The reaction was stirred at the same temperature for 5 h, then filtered into a solution of ferrous sulfate heptahydrate (132 g) and tartaric acid (40 g) in water (400 mL) at 0° C. The mixture was stirred for 20 min, then transferred to a separatory funnel and extracted with t-BuOMe (2×200 mL). The combined organic phase was stirred with 30% NaOH solution containing NaCl, for 1 h at 0° C. The layers were again separated, and the aqueous phase extracted with t-BuOMe. The combined organic phase was washed with brine, dried over $MgSO_4$ and concentrated to yield the title compound (52.8 g) as an amber oil.

Step 4

(2R,3R)-2-Hydroxy-3-methyl-5-phenylpentan-1-ol (17)

To a 5 L 3-neck round-bottom flask equipped with a mechanical stirrer, thermocouple and nitrogen inlet was added a mixture of hexanes (IL). The vessel was cooled to 0° C. A 2.0M solution of $Me_3Al$ in hexanes (800 mL, 1.6 mol) was added, followed by a solution of epoxide 16 (120 g, 0.677 mol) in hexanes (250 mL)/$CH_{12}C_{12}$ (50 mL), maintaining the temperature below 20° C. Upon complete addition, the cloudy reaction mixture was stirred at 5° C. for 35 min. Then a solution of 10% HCl (300 mL) was added dropwise, followed by the addition of conc HCl (350 mL). The layers were separated, and the organic phase was washed with brine and dried over $MgSO_4$. After removal of the volatiles in vacuo, the title compound (122.1 g) was obtained as an oil.

Step 5

(2R,3R)-2-Hydroxy-3-methyl-5-phenylpent-1-yl Tosylate (18)

To a 2 L 3-neck round-bottom flask equipped with a mechanical stirrer and nitrogen inlet was added diol 17 (58 g, 0.30 mol), dibutyltin oxide (1.5 g, 0.006 mol, 2 mol %), p-toluenesulfonyl chloride (57.5 g, 0.30 mol), $CH_2Cl_2$ (580 mL) and triethylamine (42.0 mL, 0.30 mol). The resulting mixture was stirred at room temperature for 2 h (although the reaction was complete within 1 h), filtered, washed with water and dried over $MgSO_4$. Concentration of the volatiles in vacuo afforded the title compound (104.1 g) as a slightly amber oil.

Step 6

(2R,3R)-2-(tert-Butyldimethylsilyloxy)-3-methyl-5-phenylpent-1-yl Tosylate (19)

A solution of tosylate 18 (100 g, 0.29 mol) and triethylamine (81.0 mL, 0.58 mol) in $CH_2Cl_2$ (1200 mL) was treated with neat TBS-OTf (99 mL, 0.43 mol) dropwise with continued stirring for another 20 min. The reaction was washed twice with brine, dried over $MgSO_4$ and concentrated to dryness. The oil was dissolved in a minimal amount of hexanes and filtered over a silica pad, eluting with hexanes:EtOAc (9:1) to yield the title compound as a slightly amber oil, 134 g.

Step 7

(2R,3R,5RS)-2-(tert-Butyldimethylsilyloxy)-3-methyl-5-bromo-5-phenylpent-1-yl Tosylate (20)

To a 5 L 3-neck round-bottom flask equipped with a mechanical stirrer, reflux condenser and nitrogen inlet was added $CCl_4$ (1680 mL), tosylate 19 (140 g, 0.30 mol), NBS (65 g, 0.365 mol) and AIBN (16.5 g, 0.10 mol). The mixture was degassed by evacuation under full vacuum with stirring, and backfilling with nitrogen (3×). The reaction mixture was then heated to reflux, whereupon the color became dark brown. After 15 min at vigorous reflux, the reaction mixture became light yellow, and chromatographic analysis indicated the reaction was complete. After cooling to room temperature, the reaction was filtered, and the filtrate was concentrated to dryness. The residue was redissolved in hexanes, filtered again, and concentrated to dryness to afford the title compound (170.3 g) as an amber oil.

Step 8

(2R,3R)-2-(tert-Butyldimethylsilyloxy)-3-methyl-5-phenylpent-4 (E)-en-1-yl Tosylate (21)

To a 2 L 3-neck round-bottom flask equipped with a mechanical stirrer, reflux condenser and nitrogen inlet was added a solution of bromide 20 (100 g, 0.186 mol) in acetonitrile (700 mL). DBU (83.6 mL, 0.557 mol) was added, and the resulting dark brown solution was stirred at reflux for 15 min. After cooling to room temperature, the solvent was removed in vacuo, and the residue digested in $CH_2Cl_2$ (200 mL) and filtered through a silica pad. The volatiles were again evaporated, and the residue dissolved in EtOAc and washed with water, brine and dried over $MgSO_4$ and concentrated to dryness. Preparative hplc (Prep 500) chromatography afforded the desired unsaturated title compound (50.3 g, 60% yield over 4 steps).

Step 9

(3S,4R)-3-(tert-Butyldimethylsilyloxy)-4-methyl-6-phenylhex-5 (E)-en-1-nitrile (22)

Tosylate 21 (50 g, 0.11 mol) was dissolved in DMSO (1 L) and treated with KCN (14.2 g, 0.22 mol) and water (25 mL). The resulting mixture was stirred at 60° C. under nitrogen for 18 h. After cooling to room temperature, the reaction mixture was partitioned between EtOAc (1 L) and water (1 L). The aqueous phase was extracted with EtOAc (500 mL), and the combined organic phase was washed with brine and dried over Na$_2$SO$_4$. Flash chromatography over silica with CH$_2$Cl$_2$ afforded the desired nitrile (22) in 92% yield.

Step 10

Methyl (5S,6R)-5-(tert-Butyldimethylsilyloxy)-6-methyl-8-phenylocta-2 (E),7 (E)-dienoate (1)

Nitrile 22 (14.67 g, 46.5 mmol) was dissolved in toluene (200 mL) and cooled to −78° C. under nitrogen. A 1.5M solution of DIBAL in toluene (37.2 mL, 55.8 mmol) was added dropwise with vigorous stirring. Upon complete addition, the cooling bath was removed, and the reaction was stirred at room temperature for 1 h. The reaction mixture was carefully poured into 1N HCl and the mixture stirred at room temperature for 30 min. The layers were separated, and the organic phase was washed with a saturated aqueous solution of sodium potassium tartrate (2×), brine and dried over Na$_2$SO$_4$. The volatiles were removed in vacuo, and the crude pale yellow oil was used directly in the subsequent condensation.

The crude aldehyde from above was dissolved in THF (90 mL) and treated with trimethyl phosphonoacetate (9.03 mL, 55.8 mmol) and TMG (7.0 mL, 55.8 mmol) at room temperature under nitrogen. The reaction mixture was stirred for 16 h, then partitioned between EtOAc (200 mL) and water (100 mL). The aqueous phase was back extracted with EtOAc (100 mL), and the combined organic phase was washed with water, brine and dried over Na$_2$SO$_4$. The volatiles were removed in vacuo, and the crude yellow oil (17.0 g) was chromatographed over silica gel with CH$_2$Cl$_2$:cyclohexane (1:1 to 2:1) to afford 13.67 grams of the desired ester 1, 78.5%.

Preparation 2

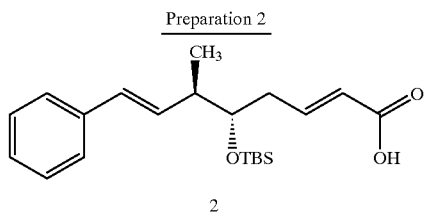

2

Methyl ester 1 (2.673 mmol) was dissolved in acetone, and then 1N aqueous LiOH (26 mL) was added at room temperature. The cloudy mixture was further diluted with acetone (20 mL), and the resulting yellow mixture was stirred at room temperature for 23.5 h. The reaction mixture was diluted with diethyl ether (400 ml), and the organics washed with iN HCl (120 mL), brine (200 mL) and H$_2$O (160 mL). The organics were dried and concentrated in vacuo to give a yellow oil which was purified by column chromatography (gradient: 5% AcOH+20%–40% EtOAc/hexanes to give carboxylic acid 2 as a yellow oil (960 mg, 100%). $^1$H NMR (CDCl$_3$) d 7.38–7.19 (m,PhH$_5$), 7.09 (ddd,J=15.2, 7.6 and 7.9 Hz, 3-H), 6.38 (d,J=16 Hz,8-H), 6.16 (dd,J=16 and 8 Hz, 7-H), 5.85 (d,J=15.8 Hz,2-H), 3.81–3.75 (m,5-H), 2.49–2.37 (m,6-H,4-CH$_2$), 1.12 (d,J=6.7 Hz,6-Me), 0.91 (s,SiCMe$_3$), 0.065 (s,SiMe), 0.068 (s, SiMe) ppm;
IR γ (CHCl$_3$) 2957,2930,2858,1697,1258,1098,838 cm$^{-1}$;
MS (FD) 360.2 (M+, 100);
[α]$_D$ +87. 60° (c 10.5, CHCl$_3$);
Anal. calcd. for C$_{21}$H$_{32}$O$_3$ requires: C, 69.95; H, 8.95%. Found: C, 69.19; H, 8.39%.

EXAMPLE 1

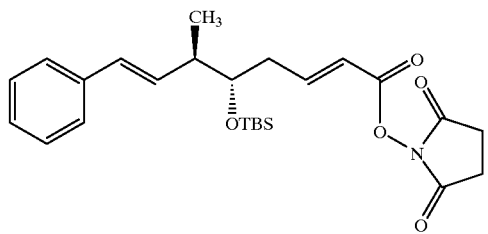

3

To a stirred solution of carboxylic acid 2 (2 mmol) in dry DMF (5.50 mL) was added 1-ethyl-3-(3-dimethyaminopropyl)carbodiimide (EDCI) (2.4 mmol) and N-hydroxysuccinimide (2.6 mmol) at room temperature. The mixture was stirred for 28 h and then diluted with EtOAc (100 mL) and washed with 1N aqueous HCl (2×50 mL), H$_2$O (75 mL), dried and concentrated in vacuo to give an oil. The crude product was purified by column chromatography (gradient: 5–30% EtOAc/hexanes) to give active ester 3 as a pale yellow oil (724 mg, 80%).
$^1$H NMR (CDCl$_3$) d 7.36–7.20 (m,PhH$_5$,3-H), 6.38 (d,J= 16 Hz,8-H), 6.14 (dd,J=16.1 and 8.0 Hz,7-H), 6.03 (d,J=16 Hz,2-H), 3.79 (q,J=4.3 Hz,5-H), 2.94 (brs,CH$_2$CH$_2$), 2.58–2.42 (m,6-H,4-CH$_2$), 1.10 (d,J=6.8 Hz,6-Me), 0.90 (s,SiCMe$_3$), 0.05 (s,SiMe$_2$) ppm;
IR γ (CHCl$_3$) 2957,2931,2858,1772,1741,1648,1364, 1254,1092,1069,838 cm$^{-1}$;
MS (FD) 457 (M+, 100);
[α]$_D$ +71.3° (c 10.1, CHCl$_3$);
Anal. calcd. for C$_{25}$H$_{35}$NO$_5$ requires: C, 65.61; H, 7.71; N, 3.06%.
Found: C, 65.51; H, 7.56; N, 3.02%.

EXAMPLE 2

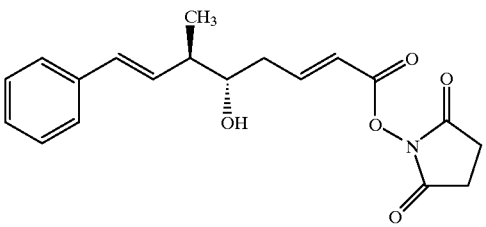

4

To a stirred solution of silyl ether 3 (2.50 g,5.47 mmol) in CH$_3$CN (130 mL) was added 48% aqueous HF (15 mL) at 0° C. The solution was stirred at 0° C. for 0.75 h and then at room temperature for 4 h. The reaction was diluted with diethyl ether (300 mL) and washed with H$_2$O until the wash was ~pH 7. Organics were dried (MgSO$_4$) and concentrated in vacuo to give a yellow residue which was recrystallized from Et$_2$O to give alcohol 4 as white crystals (1.46 g,78%).
$^1$H NMR (CDCl$_3$) d 7.41–7.20 (m,PhH$_5$,3-H), 6.48 (d,J= 16 Hz, 8-H), 6.15–6.07 (m,7-H, 2-H),3.71–3.65 (m,5-H), 2.83 (brs,CH$_2$CH$_2$), 2.60–2.33 (m,6-H,4-CH$_2$), 1.95 (brs, 5-OH), 1.14 (d,J=6.8 Hz,6-Me) ppm;
IR γ (KBr) 3457,1804,1773,1735,1724,1209,1099,1067, 1049,975,744,694 cm$^{-1}$;
UV (EtOH) $\lambda_{max}$ 250 (ε=20535) nm;
MS (FD) 343.2 (M$^+$, 100);
[α]$_D$ −57.8° (c 10.56, CHCl$_3$);
Anal. calcd. for C$_{19}$H$_{21}$NO$_5$S requires: C, 66.46; H, 6.16; N, 4.08%. Found: C, 66.49; H, 6.16; N, 4.07%.

EXAMPLE 3

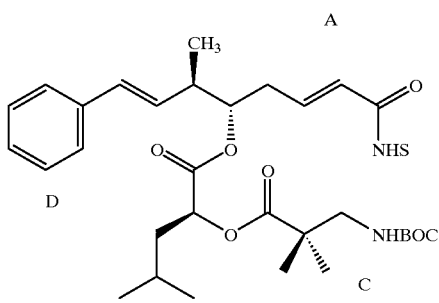

To a suspension of carboxylic acid 5 (1.28 g, 3.87 mmol), in dry dichloromethane (6 mL) was added EDCI (742 mg,3.87 mmol) and DMAP (73 mg,0.60 mmol), and the mixture was stirred at room temperature for 0.5 h. A solution of alcohol 4 (1.02 g, 2.97 mmol) in dichloromethane (5.5 mL) was added to the reaction mixture and stirred for a further 0.3 h. The reaction was diluted with $CH_2Cl_2$ (200 mL) and washed with 1N aq. HCl (2×50 mL), sat. aq. $NaHCO_3$ (2×50 mL) and $H_2O$ (50 mL). The organics were dried ($MgSO_4$) and concentrated in vacuo to leave an oily residue, which was purified by column chromatography (gradient: 10–30% EtOAc/hexanes) to give the desired ester 6 as a yellow solid (1.68 g,79%).

$^1$H NMR ($CDCl_3$) unit A d 7.35–7.20 (m, $PhH_5$, 3-H), 6.43 (d,J=15.8 Hz,8-H), 6.12 (d,J=15.9 Hz, 2H), 5.99 (dd, J=8.5 and 15.8 Hz,7-H), 5.06–5.08 (m,5-H), 2.85 (brs, $CH_2CH_2$), 2.68–2.61 (m,6-H,4-$CH_2$), 1.13 (d,J=6.8 Hz,6-Me); unit C d 5.31 (brt,NH), 3.28–3.25 (m,3-$CH_2$), 1.43 (s,$CMe_3$), 1.21 (s,2-Me), 1.19 (s,2-Me); unit D d 4.95 (dd,J=9.8 and 3.8 Hz,2-H), 1.73–1.64 (m,3-H,4-H), 1.59–1.49 (m,3-HI), 0.85 (d,J=6.4 Hz,5-Me), 0.82 (d,J=6.4 Hz,4-Me) ppm;

IR γ (KBr) 3400, 2975,1743,1367,1206,1126,1145,1068 $cm^{-1}$;

MS (FD) 657 (M+,100);

$[α]_D$ +39.5° (c 10.38, $CHCl_3$);

Anal. calcd. for $C_{35}H_{48}N_2O_{10}$ requires: C, 64.01; H, 7.37; N, 4.27%. Found: C, 64.19; H, 7.27; N, 4.52%.

EXAMPLE 5

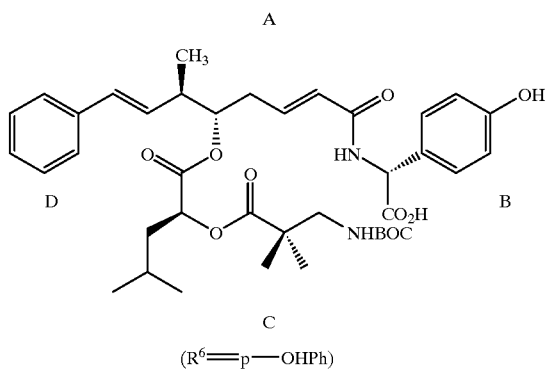

7a ($R^6$=p—OHPh)

To a stirred solution of active ester 6 (150 mg, 0.229 mmol) in dry DMF (2.5 mL) was added BSA (282 μL,1.143 mmol) followed by D-hydroxy-phenylglycine (57 mg,0.343 mmmol). The mixture was heated in a sealed tube under $N_2$ at 55° C. for 20 h. The reaction solution was diluted with EtOAc (180 mL) and washed with 1N aq. HCl (50 mL), $H_2O$ (50 mL), brine (50 mL), dried ($MgSO_4$) and concentrated in vacuo to give a yellow solid. Purification of the crude solid by column chromatography (gradient: 5–20% MeOH/$CH_2Cl_2$) provided amide 7a (122 mg,75%).

$^1$H NMR ($CD_3OD/CDCl_3$) Unit A d 7.27–7.20 (m,$PhH_5$), 6.75–6.69 (m,3-H), 6.43 (d,J=15.9 Hz,8-H), 5.96 (d,J=15.7 Hz,7-H), 5.93 (d,J=15.6 Hz,2-H), 4.95–4.93 (m,5-H), 2.56–2.49 (m,6-H,4-$CH_2$), 1.04 (d,J=6.8 Hz,6-Me); Unit B d 7.16 (d,J=8.3 Hz,$ArH_2$), 6.66 (d,J=8.2 Hz,$ArH_2$), 5.62 (brt,NH), 5.19–5.18 (m,2-H); Unit C d 3.15 (d,J=6.3 Hz,3-$CH_2$), 1.36 (s,$CMe_3$), 1.11 (s,2-Me), 1.08 (s,2-Me); Unit D d 4.85 (dd,J=9.6 and 3.3 Hz,2-H), 1.64–1.57 (m,3-H,4-H), 1.55–1.47 (m,3-H'), 0.76 (d, J=6.3 Hz,5-Me), 0.73 (d,J=6.3 Hz,4-Me) ppm;

IR γ (KBr) 3400, 2972, 1728, 1672, 1614, 1515, 1450, 1416, 1171, 1147 $cm^{-1}$;

MS (FAB) 610.6 ($[MH_2$-Boc$]^+$, 100);

$[α]_D$ −19.9° (c 6.53, MeOH).

EXAMPLE 6

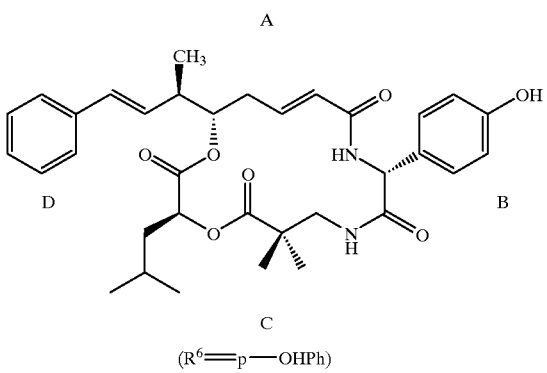

8a ($R^6$=p—OHPh)

The BOC amine 7a, as prepared by Example 5 (109 mg,0.154 mmol), was dissolved in trifluoroacetic acid (5 mL,5 mM) and stirred at room temperature for 2 h. The reaction was concentrated in vacuo and dried under high vacuum to give the trifluoroacetate salt of amine 7a as a light brown foam. The crude amine salt (max. 0.154 mmol) was dissolved in dry DMF (31 mL) and diisopropylethylamine (80 μL, 0.462 mmol), followed by addition of pentafluorophenyl diphenylphosphinate (77 mg,0.2 mmol). The resulting solution was stirred at room temperature under dry $N_2$ for 15 h, and concentrated in vacuo, and the residue was purified by column chromatography (gradient: 1–4% MeOH/$CH_2Cl_2$) to provide cryptophycin 8a as a tan solid (54 mg, 59%).

$^1$H NMR ($CDCl_3$) Unit A d 7.36–7.15 (m,$PhH_5$), 6.79–6.69 (m,3-H), 6.54 (d,J=15.8 Hz,8-H), 5.98 (dd,J=15.8 and 8.8 Hz,7-H), 5.06–5.0 (m,5-H), 2.61–2.49 (m,6-H,4-H), 2.39–2.30 (m,3-H'), 1.10 (d,J=6.8 Hz,6-Me); Unit B d 7.90 (dd,J=10 and 1.68 Hz,OH), 7.65 (d,J=6.3 Hz,NH), 7.10 (d,J=8.5 Hz,$ArH_2$), 6.71 (d,J=8.4 Hz,$ArH_2$), 5.28 (d,J=6.5 Hz,2-H); Unit C d 3.55–3.47 (dd,J=13.3 and 10.1 Hz,3-$CH_2$), 3.00 (d,J=13.4 Hz,NH) 1.19 (s,2-Me), 1.16 (s,2-Me); Unit D d 4.90 (dd,J=10 and 3.5 Hz,2-H), 1.66–1.54 (m,3-H,4-H), 1.32–1.25 (m,3-H'), 0.67 (apparent t,J=7.1 Hz,5-Me, 4-Me) ppm;

IR γ (KBr) 3418,3340,2960,1740,1713,1671,1514,1271, 1198,1155,972 $cm^{-1}$;

MS (FD) 590 (M+, 100);

$[α]_D$ +15.35° (c 3.91, $CHCl_3$).

EXAMPLE 7

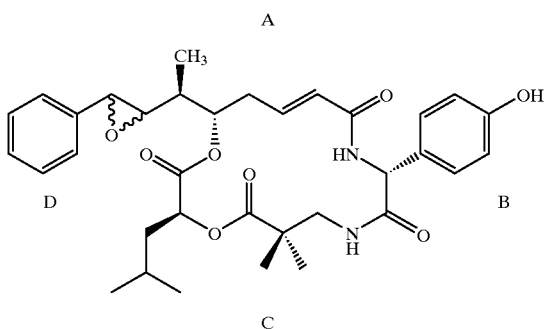

Styrene 8a, prepared as described by Example 6 (42 mg, 0.0712 mmol) was suspended in dry dichloromethane (2.2 mL, 0.035 mM), and mcpba (49 mg, 0.285 mmol) was added in one portion at room temperature. Dry tetrahydrofuran (0.3 mL) was added to produce a homogeneous solution. The reaction was stirred under $N_2$ at room temperture for 21 h and then diluted with further $CH_2Cl_2$ (15 mL). Organics were washed with 10% aq. $Na_2S_2O_5$ (10 mL), sat. aq. $NaHCO_3$ (10 mL), $H_2O$ (10 mL), dried ($MgSO_4$) and concentrated in vacuo to give a yellow solid. The crude product was initially purified by column chromatography (gradient: 1–5% $MeOH/CH_2Cl_2$) to give a 1:1.15 mixture of α:β C7–C8 epoxides as a white solid (23 mg, 54%). Reverse phase HPLC (column: 4.6×250 mm Kromsil C18; Eluent: 60% $CH_3CN/H_2O$; Flow: 1.0 mL/min; WV: 220 nm). Separation of the α:β mixture provided α-epoxide 11b' ($R^6$=p-OHPh) (2.3 mg, t=13.7 min) and β-epoxide 11a' ($R^6$=p-OHPh) (5.8 mg, t=12.1 min) as white solids.

β-Epoxide 11a'

$^1$H NMR (CDCl$_3$) Unit A d 7.36–7.16 (m,PhH5), 6.70–6.79 (m,3-H), 5.91 (dd,J=15.5 and 5.18 Hz,2-H) 5.23–5.18 (m,5-H), 3.75 (d,J=1.67 Hz,8-H), 2.96 (dd,J=7.4 and 2.0 Hz,7-H), 2.72–2.67 (m,4-H), 2.44–2.39 (m,4-H), 1.81–1.88 (m,6-H), 1.13 (d,J=6.9 Hz,6-Me); Unit B d 7.66 (s,NH), 7.13 (d,J=8.5 Hz,ArH$_2$), 6.74 (d,J=8.5 Hz,ArH2), 5.27 (s,2-H); Unit C d 7.66 (s,NH), 3.49 (dd,J=13.6 and 10 Hz,3-CH$_2$), 1.20 (s,2-Me),1.18 (s,2-Me); Unit D d 4.93 (dd,J=10 and 3.2 Hz,2-H), 1.69–1.59 (m,3-H,4-H), 1.30–1.22 (m,3-H'), 0.79 (d,J=6.2 Hz,5-Me), 0.78 (d,J=6.3 Hz,4-Me) ppm.

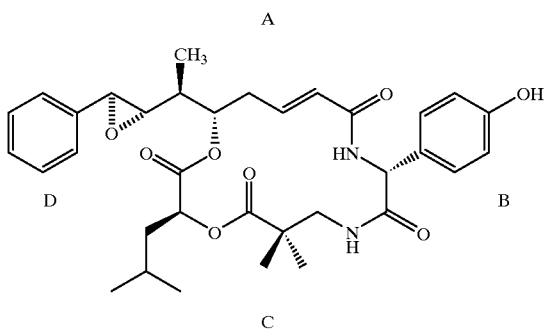

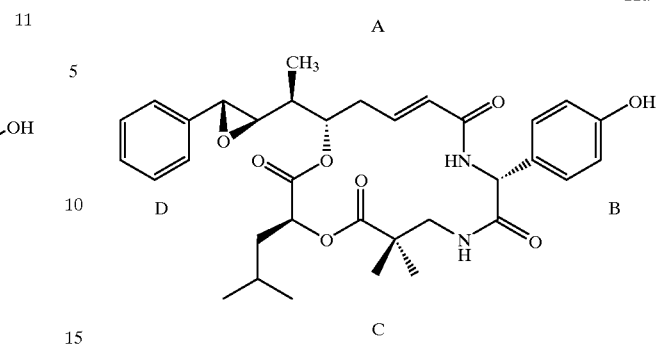

What is claimed is:

1. A compound of formula IV

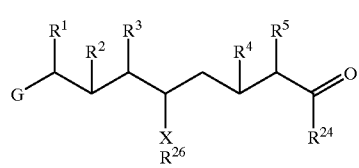

wherein

G is C1–C12 alkyl, C2–C12 alkenyl, C2–C12 alkynyl or Ar;

Ar is an aromatic or heteroaromatic group or a substituted aromatic or heteroaromatic group;

$R^1$ is halo, SR, OR, amino, mono or di-($C_1$–$C_6$-alkyl) amino, tri($C_1$–$C_6$-alkyl)ammonium, $C_1$–$C_6$-alkylthio, di($C_1$–$C_6$-alkyl)sulfonium, $C_1$–$C_6$-alkylsulfonyl, or $C_1$–$C_6$-alkylphosphonyl;

R is H, $C_1$–$C_6$ alkyl, $C_2$–$C_6$ alkanoyl or Ar; and $R^2$ is OH or SH; or $R^1$ and $R^2$ taken together form a second bond or together form an epoxide, aziridine, episulfide, or cyclopropyl ring;

$R^3$ is $C_1$–$C_6$ alkyl;

$R^4$ and $R^5$ are H; or $R^4$ and $R^5$ taken together form a second bond;

$R^{24}$ is a leaving group; and $R^{26}$ is an alcohol protecting group;

X is O, NH or (C1–C3 alkyl)N—.

2. A compound of claim 1 wherein G is phenyl.

3. A compound of claim 1 wherein $R^1$ and $R^2$ together form an epoxide ring.

4. A compound of claim 1 wherein $R^4$ and $R^5$ together form a second bond.

5. A compound of claim 1 wherein $R^{24}$ is —NHS.

* * * * *